US00PP27949P2

(12) United States Plant Patent
Horvath

(10) Patent No.: US PP27,949 P2
(45) Date of Patent: Apr. 25, 2017

(54) ***ANDROPOGON GERARDII* PLANT NAMED 'BLACKHAWKS'**

(50) Latin Name: *Andropogon gerardii*
Varietal Denomination: Blackhawks

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 14/757,300

(22) Filed: Dec. 15, 2015

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para

(57) ABSTRACT

A new, distinct *Andropogon gerardii* plant as shown and described, characterized by a more upright plant with a height of 150 cm or less, dark green colored foliage with purple-red tips and joints, and purple fall color that turns deep purple, compared to parent plant.

1 Drawing Sheet

Latin name: *Andropogon gerardii.*
Cultivar name: 'Blackhawks'.

BACKGROUND OF THE INVENTION

The present invention relates to a new form of *Andropogon gerardii* plant named 'Blackhawks'. 'Blackhawks' is a seedling of *Andropogon gerardii* 'Red October', United States plant patent applied for, characterized by a more upright plant with a height of 150 cm or less, dark green colored foliage with purple-red tips and joints, and purple fall color that turns deep purple, compared to dark green colored foliage and the taller habit of 170 cm of the parent plant. The new plant was grown as a seedling of *Andropogon gerardii* 'Red October', United States plant patent applied for, by the inventor at a wholesale perennial nursery in Hebron, Ill. USA in 2012. The selection of this plant was due to its thicker stems, height of 150 cm or less, and dark green colored foliage with purple-red tips and joints, and purple fall color that turns deep purple. Asexual, vegetative division propagation has been the only means of reproduction. Propagation has taken place at Hebron, Ill. since 2013. In 2015 we planted 1500 plants in 1 gallon pots. To date these plants have remained uniform in height, and foliage color. The new *Andropogon gerardii* has shown to be stable and identical in reproduction to the parent after making over 1500 vegetative divisions from 2013 to 2015.

SUMMARY OF THE INVENTION

In the following description, color references are made to The Royal Horticultural Society Colour Chart (copyright 2001). The new *Andropogon gerardii* plant named 'Blackhawks' has shown the characteristics of a more upright plant height of 150 cm or less, and dark green colored foliage with purple-red tips and joints, and purple fall color that turns deep purple to be unique and stable. For purpose of the comparison the new plant will be referred to as 'Blackhawks'.

Plants of 'Blackhawks' can be compared to plants of *Andropogon gerardii* 'Indian Warrior', U.S. Plant Pat. No. 24,999. 1. 'Blackhawks' has upright growth and a height of 150 cm or less compared to the height of *Andropogon gerardii* 'Indian Warrior' which has an average height of 150-180 cm. 2. 'Blackhawks' has a foliage color of green 147 A coloring to N 186 A compared to *Andropogon gerardii* 'Indian Warrior' which has foliage color of green 137 A coloring to N 77 A.

Plants of 'Blackhawks' can be also be compared to plants of *Andropogon gerardii* 'Red Bull' not patented. 1. 'Blackhawks' has a height of 150 cm or less compared to the height of *Andropogon gerardii* 'Red Bull which has an average height of 180-210 cm. 2. 'Blackhawks' has a foliage color of green 147 A coloring to N 186 A compared to *Andropogon gerardii* 'Red Bull' which has foliage color that is, close to RHS 136 C. 3. 'Blackhawks' has a uniform red fall color 183 D and is propagated by division while the *Andropogon gerardii* 'Red Bull' has a variable orange red fall color and is propagated by seed.

DESCRIPTION OF PHOTOGRAPHS

Figure 1:
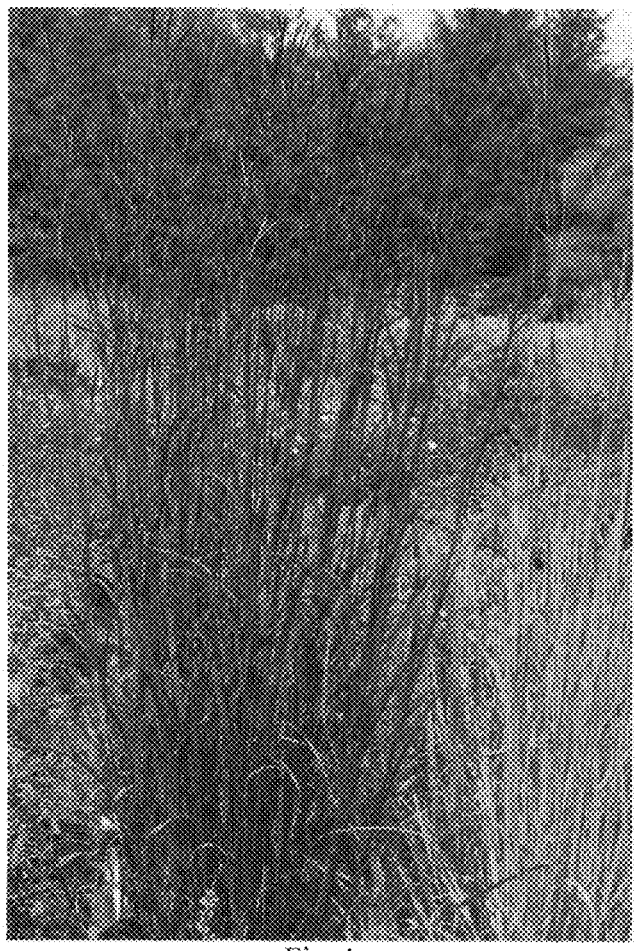

FIG. 1. Shows a plant Blooming in August with green and purple foliage.

Figure 2:
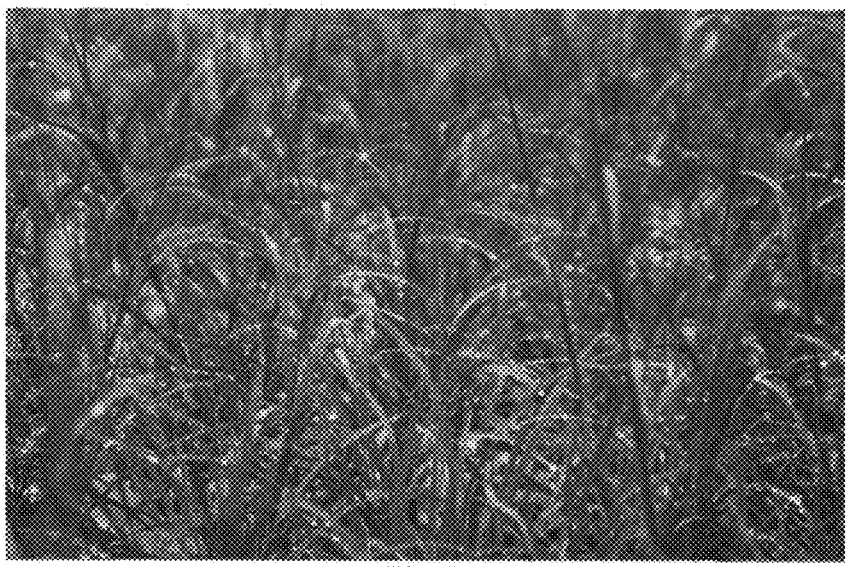

FIG. 2. Shows a plant in September with purple fall foliage color.

DETAILED BOTANICAL DESCRIPTION

In the following description, color references are made to The Royal Horticultural Society Colour Chart. The plant herein described is an established 2 year old plant growing in a garden, grown in full sun and irrigated in Hebron, Ill. USA. Measurements and numerical values represent averages of typical plants.

Botanical classification: *Andropogon gerardii* cultivar 'Blackhawks'.

Parentage: *Andropogon gerardii* 'Red October' seedling.

Propagation: Vegetative division.

Plant description: Overall habit of the new *Andropogon* is clumping with upright culms topped by red colored flowers beginning in August. Vigor is moderate.

*Plant height*.—150 cm.

*Plant width*.—60-75 cm.

Foliage and stems:

*Foliage description*.—Glabrous, flat blade, sheathed from node of attachment to ligule, linear.

*Type*.—Deciduous, grass growing in culms.

*Shape*.—Blade.

*Sheath*.—17 mm wide, 19 cm long, surface — glabrous.

*Ligules*.—Up to 1 mm long and up to 6 mm wide.

*Number of blades*.—Typically 7 blades per stem.

*Blade length*.—10-11 mm wide, up to 50 cm long, ranging from 40 to 50 cm without the sheath.

*Sheath*.—17 mm wide, ranging from 7 to 16 cm long.

*Adaxial leaf description*.—Leaf color is 147 A coloring up to N 186 A.

*Abaxial leaf description*.—Leaf color is 147 A coloring up to N 186 B.

*Veins*.—Parallel, same color as surrounding leaf on both top and bottom of leaf.

*Culm description*.—Erect, cylindrical, typically up to 7 leaves.

*Culm or stem diameter*.—6 mm average, but typically 6 mm between the nodes and swelling to 7 mm at the base of the internodes.

*Color of the internodes is 59 A and B.*

*Number of culms or stems per clump*.—Over 30.

*Node description*.—Cylindrical.

*Number of nodes per culm*.—Average 7.

*Length of internodes*.—Ranges from 7-16 cm.

Flower inflorescence:

*Inflorescence type*.—Terminal raceme with sessile and pedicillate spikelets.

*Rachis*.—1 mm wide and up to 7 cm long, color N 77 A.

*Overall raceme size*.—5 cm wide, 9 cm long.

*Rames*.—Mostly 5 mm wide, 9 cm long.

*Rachilla*.—Less than 1 mm wide, 7 mm long, color starts N 77 A.

*Inflorescence color*.—As a whole the color is N 77 A.

*Spikelet*.—Sessile and pedicellate — Both 4 mm wide 9 cm long, color is N 77 A.

*Individual floret size*.—1 mm wide, 12 mm long including awn.

*Lower glume*.—2 mm wide, 13 mm long, color starts 163 B coloring up to N77A.

*Lemma*.—Outer and inner — both, wider than 1 mm less than 2 mm, 13 mm long, color N 77 A.

*Awn size*.—Is less than 1 mm wide and average 10 mm long.

*Pedicels*.—8 per, rames and are shorter toward the base of the plant, 1 mm wide and 10-15 cm long.

*Flower number*.—Approximately 15-20 florets per rames, average 50 per spikelet, mature spikelet measuring 5 cm wide, 9 cm long.

*Cynocium*.—Stigma — 2. Color close to N 77 A.

*Androecium*.—Anthers — number 3, color — is yellow 11 A. Anther size — 4 mm long by 1 mm wide.

*Fertility*.—Fertile with 3 Anthers and 3 Stamens.

*Blooming habit*.—Terminal raceme on up to 150 cm stems.

*Bloom period and duration*.—Last two weeks of August to the end of September.

*Bloom color*.—N 77 A.

*Fruit or seeds*.—Color is N 77 A, size is 1-2 mm wide, 13 mm long.

*Scent*.—No scent.

*Roots*.—Stiff, fibrous, and freely branching.

*Fruit*.—Seed identical to the species except color is darker, N 77 A.

Hardiness: United States Department of Agriculture Zones 4-9.

Disease resistance: Plants are not susceptible to any major pests or diseases.

I claim:

1. A new, distinct *Andropogon gerardii* plant as shown and described, characterized by a more upright plant with a height of 150 cm or less, dark green colored foliage with purple-red tips and joints, and purple fall color that turns deep purple, compared to parent plant.

* * * * *